(12) United States Patent
Tsow et al.

(10) Patent No.: US 10,078,074 B2
(45) Date of Patent: Sep. 18, 2018

(54) PORTABLE METABOLIC ANALYZER SYSTEM

(71) Applicants: Francis Tsow, Tempe, AZ (US); Xiaojun Xian, Gilbert, AZ (US); Erica Forzani, Mesa, AZ (US); Nongjian Tao, Scottsdale, AZ (US); ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

(72) Inventors: Francis Tsow, Tempe, AZ (US); Xiaojun Xian, Gilbert, AZ (US); Erica Forzani, Mesa, AZ (US); Nongjian Tao, Fountain Hills, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 447 days.

(21) Appl. No.: 14/761,732

(22) PCT Filed: Jan. 21, 2014

(86) PCT No.: PCT/US2014/012383
§ 371 (c)(1),
(2) Date: Jul. 17, 2015

(87) PCT Pub. No.: WO2014/116604
PCT Pub. Date: Jul. 31, 2014

(65) Prior Publication Data
US 2015/0369795 A1 Dec. 24, 2015

Related U.S. Application Data

(60) Provisional application No. 61/755,319, filed on Jan. 22, 2013.

(51) Int. Cl.
*A61B 5/083* (2006.01)
*A61B 5/0482* (2006.01)
(Continued)

(52) U.S. Cl.
CPC ......... *G01N 33/497* (2013.01); *A61B 5/0482* (2013.01); *A61B 5/083* (2013.01);
(Continued)

(58) Field of Classification Search
CPC .... G01N 33/497; A61B 5/0482; A61B 5/083; A61B 5/087; A61B 5/7405; A61B 5/0816
(Continued)

(56) References Cited

U.S. PATENT DOCUMENTS 4,631,966 A 12/1986 Brugnoli
4,658,832 A 4/1987 Brugnoli
(Continued)

FOREIGN PATENT DOCUMENTS

WO WO2004041084 A1 5/2004
WO WO2010143027 A1 12/2010
WO WO2013009589 A1 1/2013

OTHER PUBLICATIONS

International Application No. PCT/US/20141012383, International Search Report, dated May 21, 2014.
(Continued)

*Primary Examiner* — Navin Natnithithadha
(74) *Attorney, Agent, or Firm* — George A. Leone; Citadel Patent Law

(57) ABSTRACT

A system for measuring and tracking metabolic rate, physical activity and calorie intake. The metabolic rate is measured with a design that features an adaptive sampling mechanism for accurate breath sample collection, optimized flow rate measurement for minimizing backpressure while maximizing accuracy, humidity regulation and water con-
(Continued)

Side View densation reduction mechanism for reliable performance, as well as breath temperature measurement for volume and humidity corrections. The system further comprises an improved algorithm for determining physical activity such as related energy expenditure, and a mechanism for tracking changes in food intake over time.

28 Claims, 13 Drawing Sheets

(51) Int. Cl.
*A61B 5/087* (2006.01)
*G01N 33/497* (2006.01)
*A61B 5/00* (2006.01)
*A61B 5/08* (2006.01)

(52) U.S. Cl.
CPC ............ *A61B 5/087* (2013.01); *A61B 5/7405* (2013.01); *A61B 5/0816* (2013.01)

(58) Field of Classification Search
USPC ................................................. 600/529–543
See application file for complete search history.

(56) References Cited

U.S. PATENT DOCUMENTS

| | | | |
|---|---|---|---|
| 4,900,514 A * | 2/1990 | Fuller | A61B 5/097 285/328 |
| 4,917,108 A | 4/1990 | Mault | |
| 5,038,792 A | 8/1991 | Mault | |
| 5,178,155 A | 1/1993 | Mault | |
| 5,419,326 A | 5/1995 | Harnoncourt | |
| 5,562,101 A | 10/1996 | Hankinson et al. | |
| 5,647,370 A | 7/1997 | Harnoncourt et al. | |
| 5,645,071 A | 8/1997 | Harnoncourt et al. | |
| 5,705,735 A | 1/1998 | Acorn | |
| 5,789,660 A | 8/1998 | Kofoed et al. | |
| 5,796,009 A | 8/1998 | Delsing | |
| 5,836,300 A | 11/1998 | Mault | |
| 6,206,837 B1 | 3/2001 | Brugnoli | |
| 6,468,222 B1 | 10/2002 | Mault et al. | |
| 6,475,158 B1 | 11/2002 | Orr et al. | |
| 6,478,736 B1 | 11/2002 | Mault | |
| 6,554,776 B1 * | 4/2003 | Snow | A61B 5/222 482/9 |
| 7,108,659 B2 | 9/2006 | Ross et al. | |
| 7,285,090 B2 * | 10/2007 | Stivoric | A61B 5/01 128/905 |
| 7,392,193 B2 | 6/2008 | Mault | |
| 8,361,801 B2 * | 1/2013 | Lanier, Jr. | A61B 5/0833 436/127 |
| 2002/0029003 A1 | 3/2002 | Mace et al. | |
| 2002/0133378 A1 | 9/2002 | Mault et al. | |
| 2002/0138213 A1 | 9/2002 | Mault | |
| 2002/0173728 A1 | 11/2002 | Mault | |
| 2003/0163321 A1 * | 8/2003 | Mault | A61B 5/044 704/270 |
| 2004/0176698 A1 | 9/2004 | Robergs et al. | |
| 2004/0254501 A1 | 12/2004 | Mault | |
| 2008/0004542 A1 | 1/2008 | Allen et al. | |
| 2009/0056409 A1 | 4/2009 | Howard et al. | |
| 2009/0170664 A1 | 7/2009 | Shirasaki et al. | |
| 2010/0036272 A1 | 2/2010 | Orr et al. | |
| 2010/0041062 A1 * | 2/2010 | Lanier, Jr. | A61B 5/0833 435/7.1 |
| 2011/0009764 A1 * | 1/2011 | Lanier | A61B 5/0833 600/532 |
| 2014/0128691 A1 * | 5/2014 | Olivier | A61B 5/0833 600/301 |
| 2015/0032019 A1 * | 1/2015 | Acker | A61B 5/082 600/532 |

OTHER PUBLICATIONS

International Application No. PCT/US/2014/012383, Written Opinion, dated May 21, 2014.
International Application No. PCT/US/20141012383, Preliminary Report on Patentability, dated Jul. 28, 2015.
European Application No. 14743429.4, Extended European Search Report, dated Oct. 4, 2016.
European Application No. 14743429.4, Communication Pursuant to Rule 70(2) and 70a(2) EPC, dated Oct. 21, 2016.
European Application No. 14743429.4, Response to Communication Pursuant to Rule 70(2) and 70a(2) EPC, dated Apr. 18, 2017.

* cited by examiner

Top view

Side View

PORTABLE METABOLIC ANALYZER SYSTEM

CROSS-REFERENCE TO RELATED APPLICATIONS

The present application claims priority from U.S. provisional application No. 61/755,319, filed Jan. 22, 2013 entitled "An improved portable metabolic analyzer system." The contents the referenced provisional application is incorporated by reference.

TECHNICAL FIELD

The present invention relates to the field of breath analyzers, and, more particularly, to an improved portable metabolic analyzer system for determining metabolic rate, energy expenditure, and respiratory quotient and also providing advises/suggestions for healthy lifestyles.

BACKGROUND

There exists a critical link between lifestyle, weight, and overall health. Extensive evidence has shown that lifestyle and behaviors, such as diet and physical activity, have a significant impact on the cause, prevention and treatment of many obesity-related diseases, including diabetes, high blood pressure, heart disease, and cancer. In fact, recent clinical studies have demonstrated that a modest weight loss of 5-7% can prevent or delay the development of Type 2 diabetes in high-risk individuals (Knowler W C, Barrett-Connor E, Fowler S E, Hamman R F, Lachin J M, Walker E A, et al. Reduction in the incidence of type 2 diabetes with lifestyle intervention or metformin. N Engl J Med. 2002 Feb. 7; 346(6):393-403; http://www.diabetesaustralia.com.au/PageFiles/763/Primarypreventionguideline.pdf), while weight loss associated with routine physical activity, such as walking, has been linked to better cardiac health and longer lifespan. Physiologically, weight gain occurs when total calorie intake exceeds total energy expenditure (http://www.fitbit.com/http://www.carefusion.com/medical-products/respiratory/cardiopulmonary-diagnostics/metabolic-carts-cpet-nutrition/metabolic-carts/oxycon-mobile.aspx; http://www.bodymedia.com/, http://www.actigraphcorp.com/), but maintaining a healthy energy balance requires easy and accurate methods to track energy expenditure and calorie intake.

Energy expenditure: Total energy expenditure (TEE) comprises primarily resting energy expenditure (REE), or known as resting metabolic rate or simply, metabolism, and physical activity-related energy expenditures (PAE). For most people who spend only a few hours per week on exercises, REE is the most important portion of energy expenditure, counting for more than 80% of TEE. One of the most accurate and frequently used methods to measure REE is indirect calorimetry, which is the gold standard method recommended by the American College of Sports Medicine, American Dietetic Association and World Health Organization. Indirect calorimetry measures the oxygen consumption and carbon dioxide production rates while breathing. However, successful and traditional indirect calorimetry relies on bulky, expensive, and difficult-to-operate equipment, which limits its applications for individuals in real-world conditions (e.g., at home, work, or in the gym). The limited portable versions of existing indirect calorimetry devices are still expensive and the results can be highly operator-dependent, necessitating the guidance of a trained professional. Mault et al. disclosed several designs of portable devices (U.S. Pat. Nos. 6,468,222 B1; 4,917,108; 5,038,792; 5,178,155; 5,179,958; and 5,836,300) to measure REE based on indirect calorimetry. These patents feature generally specific flow designs for passing both inhalations and exhalations of the user, and inclusion of a scrubber to remove $CO_2$ from breath to determine oxygen consumption. Orr et al. (U.S. Pat. No. 6,475,158 B1) disclosed a design of metabolic analyzer including a mixing chamber and calibration gas to measure oxygen consumption. In addition, Kofoed et al. disclosed a different flow design to measure flow rate and infrared detection chamber to measure $CO_2$ production in breath (U.S. Pat. No. 5,789,660). Tao and Forzani (PCT 13/493,552) disclosed a portable metabolic analyzer based on a colorimetric sensing technology to track REE. However, in order to accurately determine REE, one must create innovative methods to quickly and correctly collect breath sample, accurately measure the flow rate of breath, monitor the temperature of breath, and mitigate water condensation issue in the portable device.

PAE tracking traditionally relies on self-reporting, which is tedious and inaccurate. More recently, physical sensors, such as accelerometers and GPS trackers, and heart rate monitors (Zhu, F. Q., M. Bosch, et al. (2010), John, D., S. Liu, et al. (2011)) have been used to track different activities. Each sensor can track certain types of physical activities, but none of them can monitor all types of physical activities. For example, the accelerometer-based sensors cannot detect physical activities, such as weight lifting and light office work-related activities while sitting on a desk, and GPS trackers do not work well for indoor activities due to limited satellite signals. There is a need to track physical activities that cannot be measured with the current physical sensors. From the type, intensity and time duration of each physical activity, the associated PAE is determined with various algorithms. For a given type, intensity and time duration of a physical activity (e.g. running), the energy expenditure varies with the gender, weight, age, skill, and shoes of the individual, and also with road and weather conditions. To improve the accuracy of the PAE, one must improve not only the physical sensors, but also the algorithms that can correctly translate the measured physical activity into energy expenditure.

Calorie intake tracking: The traditional approach to assess calorie intake and TEE is self-reporting, which has led to important discoveries relating lifestyle behaviors to disease development. However, studies, including those by R. P. Troiano and P. S. Freedson reported in American Journal of Preventive Medicine, vol. 38, pp. 682-683, June 2010, have also revealed the pitfalls of self-reporting—there is a clear need for more quantitative and objective methods. To meet this need, new devices, smartphone, and web applications that monitor calorie intake (Zhu, F. Q., M. Bosch, et al. (2010)) and TEE (Kozey, S. L., K. Lyden, et al. (2010), Matthews, C., K. Chen, et al. (2008)) have been developed. Examples include the recording of food consumption from digital photos and videos based on image recognition algorithms. These methods are useful but still subject to errors and usability issues. Speech recognition may also be used to track calorie intake (U.S. Pat. No. 007392193B2). However, recording every item in the total calorie intake is tedious, and also subject to errors due to the person's limited ability to correctly estimate the portion of each consumed item, and accurately memorize and record every meal.

Tracking energy expenditure and calorie intake in an integrated device: To guide individuals to maintain a healthy balance between energy expenditure and calorie intake, it is highly desirable to be able to track PAE, REE, and calorie intake in an integrated system. Mault (U.S. Pat. No. 6,478, 736 B1) describes a system that tracks REE with indirect calorimetry, physical activities and food consumption provided by the user, and determines energy balance from the tracked REE, physical activities and food consumption. However, tracking each physical activity, and each food item consumed by the user every meal and every day is difficult for most people.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The disclosed invention features improved apparatus and method that address the unresolved issues in the prior arts described above. More specifically, it discloses 1) an adaptive sampling mechanism for accurate breath sample collection, 2) optimized flow rate measurement design for minimizing backpressure while maximizing accuracy, 3) humidity regulation and water condensation reduction mechanisms for reliable performance of the apparatus and method, as well as breath temperature measurement design for volume and humidity corrections; 4) an algorithm for determining physical activity-related energy expenditure from physical activities based on REE measurement; 5) embodiment of a voice recognition algorithm to track a change, rather than the total food consumption in the calorie intake; 6) and an algorithm for recommending physical activity to achieve target weight at a target date based on the measured REE.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 10A and FIG. 10B schematically show one embodiment of a sensor cartridge design.

Figure 1:
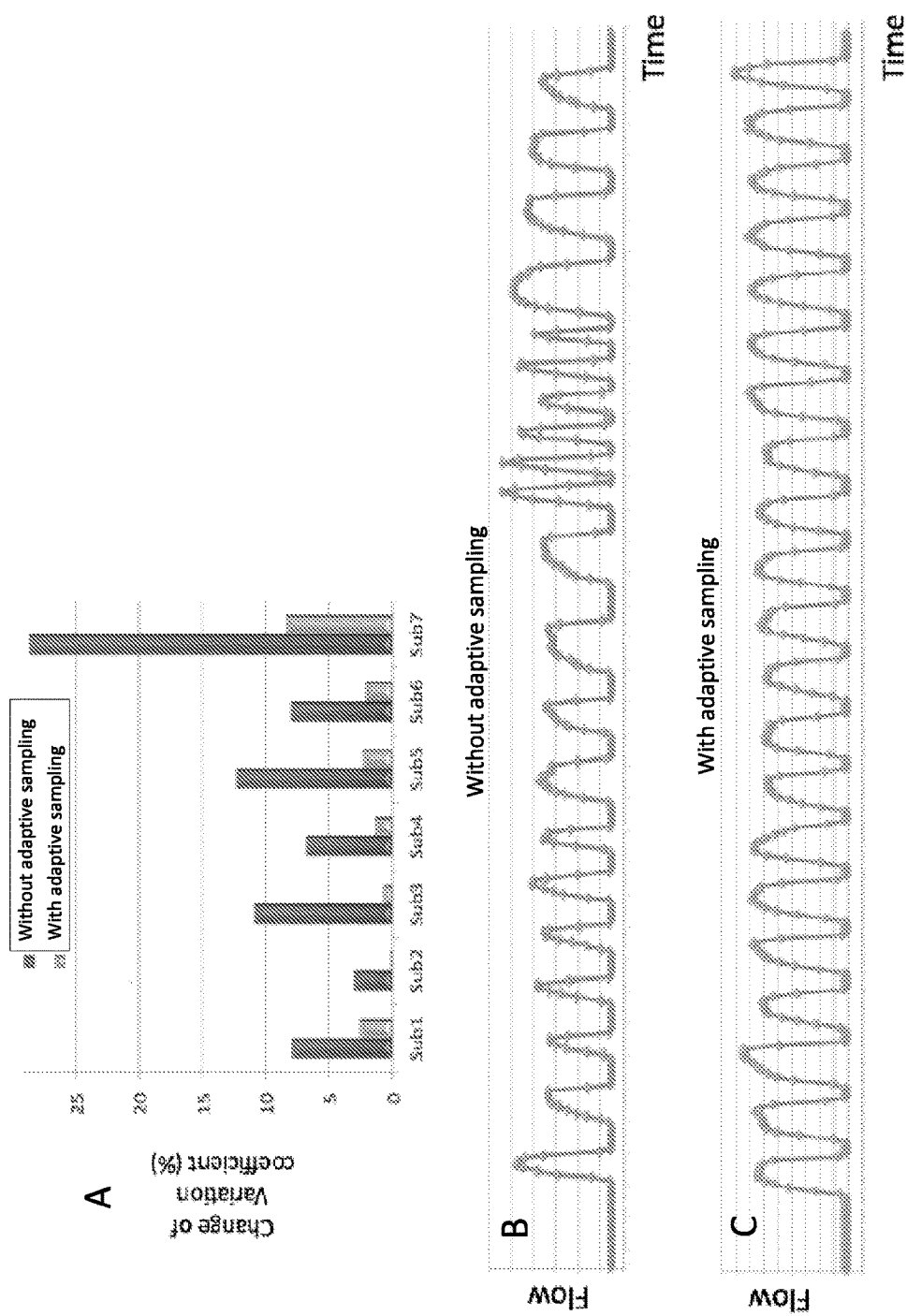
FIG. 1A shows a comparison of variations in the breathing frequency between measurements with and without an adaptive sampling mechanism for 7 subjects is graphically shown.
FIG. 1B shows breath flow rate vs. time without adaptive sampling.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments for metabolic analyzers that are based on detection of several metabolic signatures. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to a portable metabolic analyzer system. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of sample collection or analysis:

As used herein, "plurality" is understood to mean more than one. For example, a plurality refers to at least 3, 4, 5, 70, or more.

As used herein, "cellular telephone" (or "cell phone") has its generally accepted meaning and includes any portable device that can make and receive telephone calls to and from a public telephone network, which includes other mobiles and fixed-line phones across the world. It also includes mobile devices that support a wide variety of other services such as text messaging, software applications (herein also called "apps"), MMS, e-mail, Internet access, short-range wireless communications (for example, infrared and Bluetooth).

As used herein, "metabolic analyzer" is understood to mean apparatus that measures resting metabolic rate or resting energy expenditure. It may also be used under non-resting conditions.

As used herein, "breathing pattern" is understood to mean a time profile of the flow rate (pressure) of exhalation, including breathing frequency and amplitude in the flow rate or pressure.

As used herein, "regular breathing pattern" is understood to mean breathing with consistent frequency and amplitude within a time interval.

As used herein, "resting breathing pattern" is understood to mean normal breathing under resting condition.

As used herein, "natural breathing pattern" is understood to mean normal breathing under relaxed condition.

As used herein, "video motion sequence" is understood to include, but is not limited to, changes in brightness, contrast, color, and pattern of a visual object with time.

As used herein, "orifice" is understood to mean a structure with an opening in the flow path to allow and regulate breath to flow through the opening.

As used herein, "adaptive sampling method" is understood to mean an algorithm including features to detect an individual's resting breathing pattern, visually or audibly displays the resting breathing pattern guidance, and adapt possible change of the individual's resting breathing pattern over time.

As used herein, "tablet computer" has its generally accepted meaning and includes any mobile computer including a complete mobile computer, larger than a $^6$ mobile phone or personal digital assistant, integrated into a flat touch screen and primarily operated by touching the screen such as, for example, an Apple iPad® tablet computer.

Preliminarily, it should be noted that the portable metabolic analyzer system described herein for the first time features functions for:
  a) REE measurement using adaptive sampling,
  b) REE measurement using flow rate measurement,
  c) REE measurement compensating for temperature correction,
  d) REE measurement compensating for water condensation,
  e) REE measurement using a colorimetric sensor cartridge,
  f) PAE measurement using an REE based MET algorithm,
  g) A calorie-intake-based behavioral change algorithm,
  h) Personalized recommendation of physical activity time based on REE, and
  i) Metabolic age based on REE measurements.
These functions are described herein below in turn.

Figure 8:
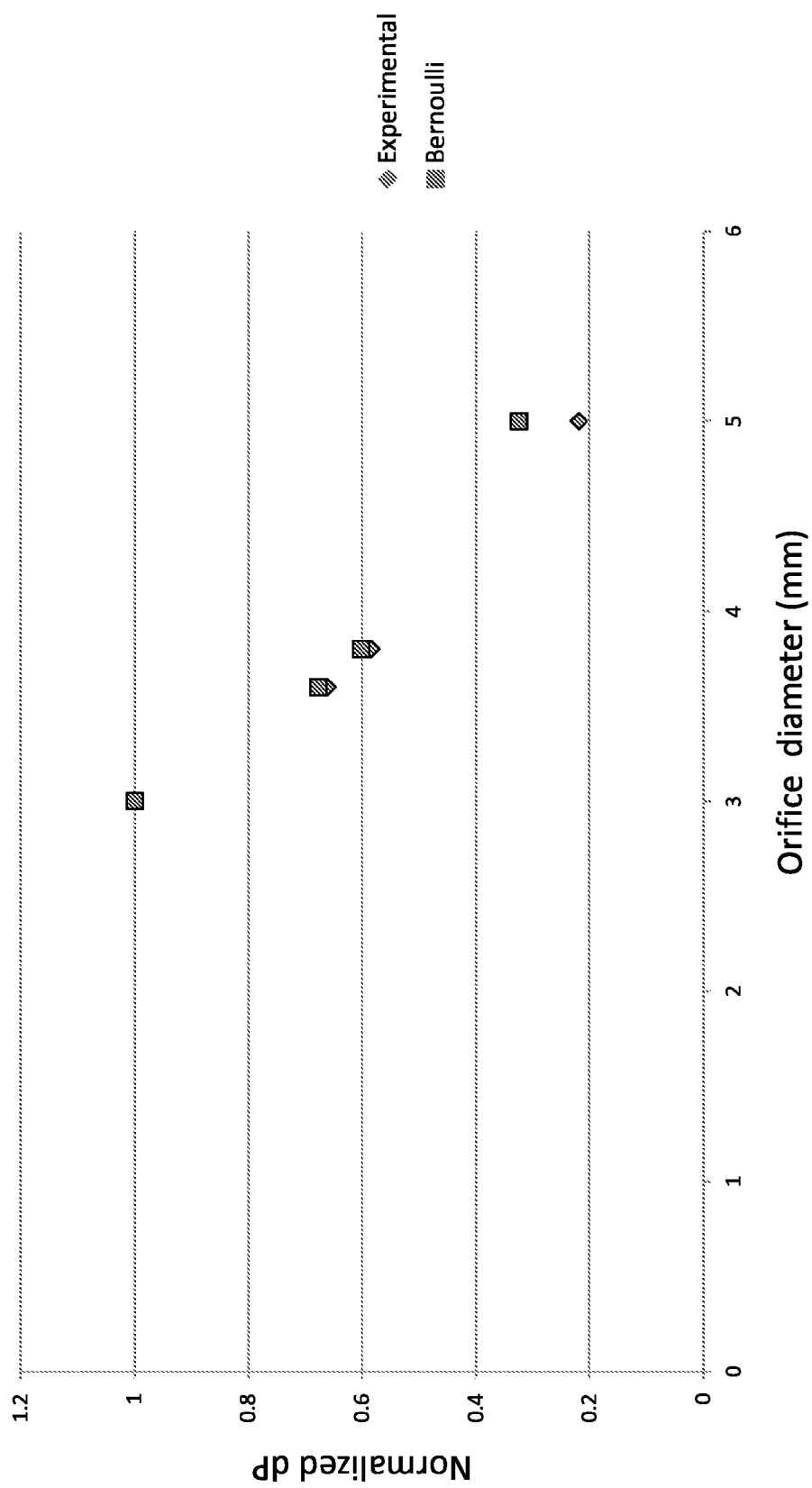
FIG. 8 illustrates dependence of normalized backpressure on the diameter of the orifice where the squares and diamonds correspond to the measured result and the calculated result from the Bernoulli equation, respectively.
Figure 9:
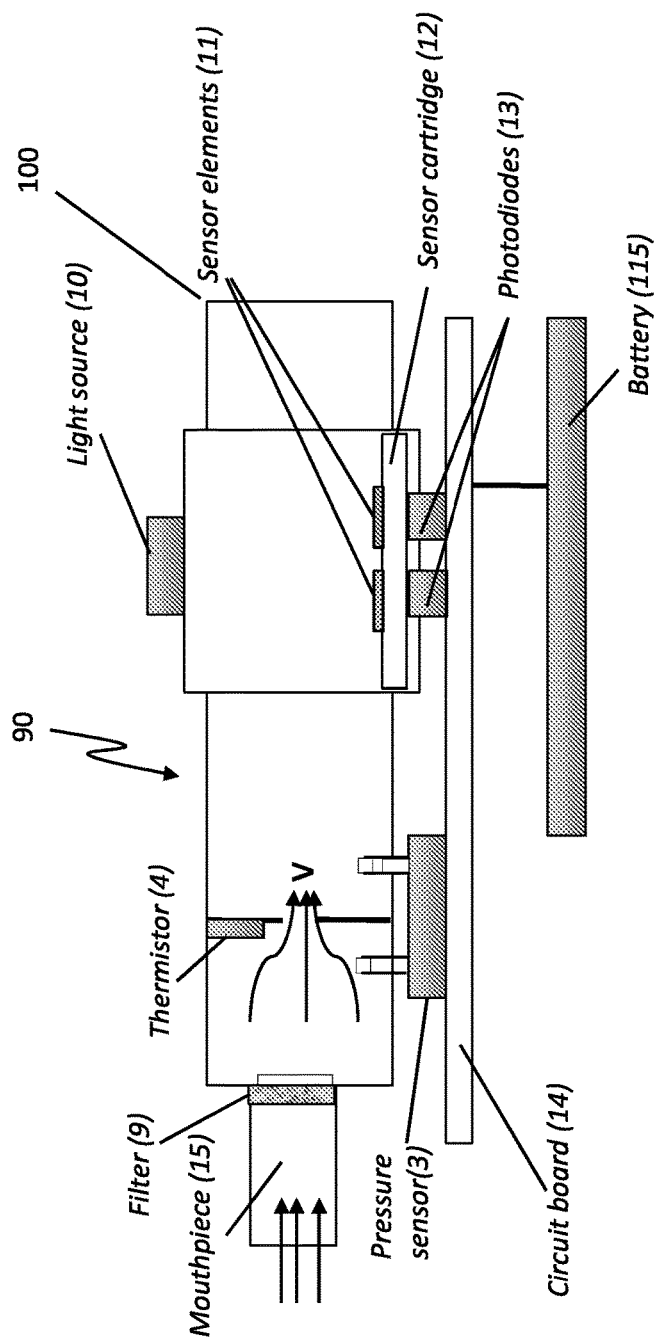
FIG. 9 schematically shows one embodiment of flow path structure of a portable metabolic analyzer system.
Figure 10:
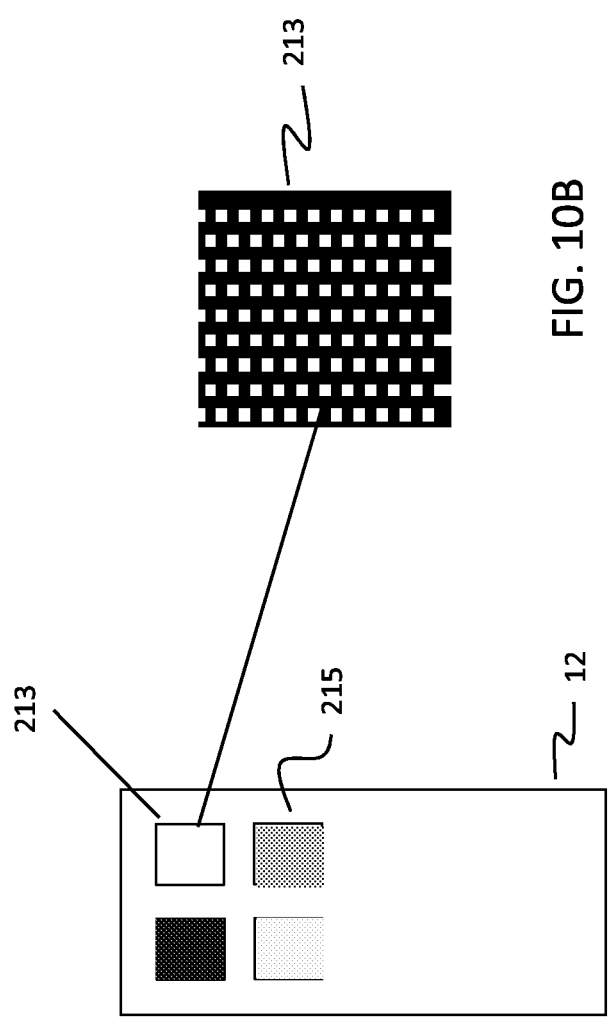
FIG. 10 shows breath flow rate vs. time with adaptive sampling.

Referring now to FIG. 1A-FIG. 10 comparison of variations in the breathing frequency between measurements with and without an adaptive sampling mechanism for 7 subjects is graphically shown. The adaptive sampling mechanism shows 3 to 12-fold improvement in the breathing frequency. FIG. 1B shows breath flow rate vs. time without adaptive sampling. FIG. 10 shows breath flow rate vs. time with adaptive sampling.

a) REE Measurement—Adaptive Sampling:

The indirect calorimetry determines REE by measuring a user's oxygen consumption rate and carbon dioxide production rate from the exhaled breath. Since REE is the energy expenditure rate of a person under resting condition, it is extremely important for the user to breath normally into the indirect calorimetry apparatus with a regular and consistent breathing frequency and amplitude (in the flow rate). Tests have shown that the measured REE values deviate from the true REE when the user breathes irregularly. For this reason, traditional REE measurement requires the guidance of a professional, and takes at least 10 minutes, making it difficult to perform REE measurement for most individuals in the everyday environment.

Extensive experiments have shown that the breathing frequency of an individual at resting condition may vary, which leads to a large variability in the measured REE values as shown in FIG. 1A-FIG. B. The present invention discloses an adaptive sampling method to ensure correct collection of breath sample by detecting and learning the user's normal breathing pattern, and then adapts possible changes of the user normal breathing pattern over time (see FIG. 1A-FIG. 10).

Mault (US Patent publication: Pub No. US 2004/0254501 A1) has disclosed a biofeedback method to assist the user to achieve relaxed state using measured metabolic rate as feedback. However, the goal of the prior art is to determine relaxed state using REE as a feedback, which is different from the present disclosure. More importantly, the present adaptive sampling method is fundamentally different from the biofeedback method, which, in general, uses instruments to measure physiological activity, such as brainwaves, heart function, breathing, muscle activity, and skin temperature, and then to rapidly 'feedback' information to the user to correct or adjust his/her activity. In other words, in the case of the biofeedback it is the user who learns to adapt him/her to the machine, which is in contrast to the case of the adaptive sampling method where it is the machine that learns to adapt the user's normal behavior.

The adaptive sampling method disclosed here has multiple benefits over the biofeedback method, which includes 1) accommodation of different breathing patterns for different individuals; 2) accommodation the change of an individual's breathing pattern over time; 3) improve user-friendliness; and 4) ensure the user breathes with a more natural pattern during the test.

In one embodiment, the user's natural breathing pattern (such as frequency and amplitude) is first pre-determined by various means. The audio rhythm and volume (and/or visual display) will be tuned to the user's natural breathing frequency, which guides him/her to exhale naturally into the mouthpiece of the metabolic analyzer for REE measurement. In order to accommodate possible changes of the user's breathing pattern and correct errors in the pre-determined breathing pattern, the adaptive sampling method memorizes the breathing patterns from previous measurements, and adjusts the audio and/or video guidance accordingly during the next measurement. An additional feature in the adaptive sampling method is to identify the time intervals, in which the breathing pattern is normal and regular during a measurement, and determine REE based on data measured during these time intervals. In the event that normal breathing pattern is not detected, the user is instructed to breathe normally, and continue the measurement until a time interval of regular and normal breathing pattern is found.

In another embodiment, the user is instructed to breathe into the apparatus naturally. The breathing pattern in the first one or several measurements is recorded, and analyzed to extract the breathing frequency and amplitude. The audio rhythm and volume (and/or visual display) will be tuned in a following measure to match the measured breathing frequency and amplitude in the first measurement, which guide him/her to breathe into the apparatus naturally in his/her second REE measurement. His/her breathing pattern in the second VE measurement is also recorded and memorized for the next measurement. This process repeats until a consistent and normal breathing pattern is detected.

This adaptive sampling method showed 3- to 12-fold improvement (see especially FIG. 1A) in the reproducibility of breathing frequency, which is critically important for the accuracy of the REE by the metabolic analyzer. An important observation is that the adaptive sampling method not only increases the reproducibility on breathing frequency but also the reproducibility of exhalation volume, and consequently, energy expenditure values. Another consequence of higher reproducibility of exhalation volume is the significant decrease of the measurement time, which is shortened from 10 min or so to less than 2 minutes. This fact increases the overall user experience during the test and enables the test to be taken in absence of a professional. FIG. 1D shows a linear correlation analysis of REE values assessed by independent users under adaptive sampling method (REEuser), and REE measures of the same users assessed by a health professional (REEProf). Four measurements were taken consecutively: two of them by the user employing the adaptive sampling method, and the remaining two by the health professional. The two measures of each kind were averaged for analysis. The high correlation of 0.95 (SD=0.01), and squared-regression coefficient of 0.9954 indicates the capability of the adaptive sampling method of capturing truly representative REE values in connection with reproducible VE, values.

b) REE Measurement—Flow Rate Measurement:

Accurate measurement of the exhaled breath volume flow rate (VE) is another critical factor for accurate REE measurement. One way to measure VE is to collect breath sample in a bag with a known volume capacity together with a timer. The volume and the timing recorded by the timer determine VE. This method measures the total breath volume over a period of time, and it does not provide breath-by-breath information (i.e., breath frequency) that is needed for the adaptive sampling method. It also requires the use of a bag, which is inconvenient for the user. Another method is to use ultrasound techniques to determine flow rate, and then determine VE from the flow rate. The ultrasound flow devices are expensive (U.S. Pat. Nos. 5,419,326; 5,503,151; 5,645,071, 5,647,370 to Hamoncort, and U.S. Pat. No. 5,796,009 to Delsing), which does not meet the requirement for personal devices. Turbine flow meters have been proposed to determine flow rate, but they are prone to errors due to inertial effects, and it is inaccurate at low flow rates (U.S. Pat. Nos. 6,206,837; 4,658,832; and 4,631,966). MEMS (Micro-electro-mechanical systems)-based pressure sensors can be used to determine flow rate and thus VE. In order to accurately measure VE with a low cost MEMS pressure sensor, correct design of the flow pathway is needed. Kofoed et al. and others describe the use of differential pressure sensor to determine flow rate for clinical applications (U.S. Pat. No. 5,789,669, PCT US 2002/0029003 A1, Orr et al., PCT, US2010/0036272 A1, W. J. Sullivan, G. M. Peters, P. L. Enright, "Pneumotachographs: Theory and Clinical Application", respiratory Care, July 1984, Vol. 29-7, pp. 736-49). However, for an affordable personal metabolic analyzer, one must be able to measure relatively low flow rate, and thus low pressure, under the resting condition accurately with a low cost pressure sensor. To meet this requirement, the flow path and flow rate measurement must be carefully designed.

Figure 2:
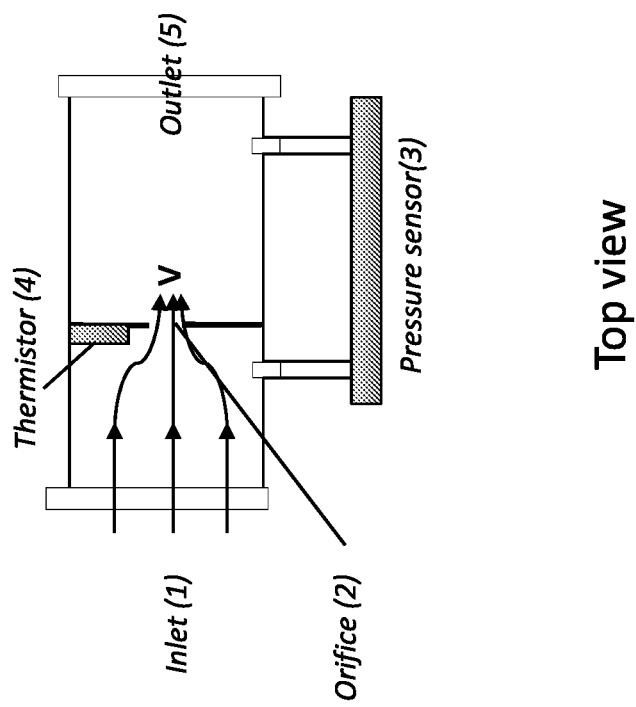
FIG. 2 shows a top view of one embodiment of flow rate measurement in the metabolic analyzer.
Figure 3:
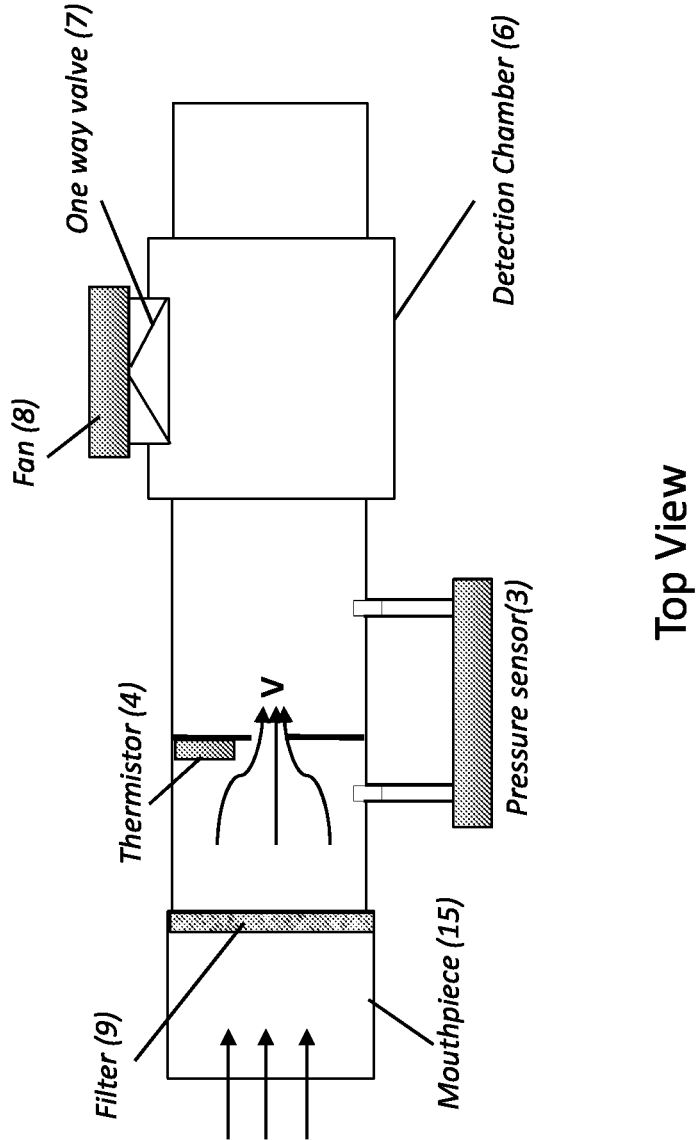
FIG. 3 shows a more detailed top view illustration of the embodiment shown in FIG. 2.

Referring now jointly to FIG. 2 and FIG. 3, a top view of one embodiment of flow rate measurement in the metabolic analyzer is shown. It features a flow path with an inlet (1) and outlet (5). The flow path includes an orifice (2) through which breath flows from the inlet to the outlet. The flow rate is determined with a pressure sensor (3) with its inlet connected to the inlet side of the orifice (2) and its outlet (5) connected to the outlet side of the orifice (2). A thermistor (4) is located near the orifice on the inlet of side of the orifice for breath temperature measurement.

Referring more specifically to FIG. 3, a more detailed illustration of the top view of the embodiment shown in FIG. 2 is illustrated. It shows a mouthpiece (15) with a filter (19) that prevents saliva from entering the flow path on the inlet side. It also shows a detection chamber (6) on the outlet side of the orifice. The detection chamber has a fan (8) connected to its side via a one-way valve (7).

The embodiments disclosed herein provide optimized geometry and dimensions to achieve accurate measurement of VE with a low cost pressure for the user to measure REE under resting conditions. The orifice separates the flow into two parts. One is connected to the mouth of the user via a mouthpiece, and the other part is connected to other parts of the breath analyzer where the pressure is the same or close to that of ambient air. Here the orifice is a key component of the system, and it is defined as an object with an opening to pass gas flow through, where the size of the opening controls the pressure difference between the two sides of the orifice, and flow velocity. The inlet of the pressure sensor is connected to the mouthpiece side, and the outlet of the pressure sensor is connected to the other side. The pressure sensor is operated in a differential detection mode such that the pressure difference between the inlet and outlet is measured. For a given flow path geometry, the pressure difference is related to volume flow rate. This can be understood by considering the Bernoulli equation, $$\Delta p = \frac{1}{2}\rho v^2$$

where p is the pressure difference, is the density of breath, and v is the flow velocity at the orifice ("2" marked in FIG. 2). Instead of the flow velocity, v, it is the exhaled volume flow rate that determines REE according to the Weir equation (see Equation 4) for REE, so one must determine VE from v, with $$V_E = \langle v \rangle A_o, \quad (2)$$

where <v> is the time average of the flow velocity at the orifice, and $A_o$ is the cross sectional area of the orifice. Since p, the backpressure, is the measured quantity, we express $V_E$ in terms of $\Delta p$ $$V_E=(2/p)^{1/2}<\Delta p^{1/2}>A_o. \quad (3)$$

According to Eq. 3, $V_E$ can be determined from the measured p vs. time, but this is only approximately correct. In practice, an experimental calibration curve that relates v vs. p is obtained by measuring p at various v. Knowing the calibration curve, v is determined from the measured p, and then Eq. 2 is used to determine $V_E$ by integrating v over time.

Figure 4:
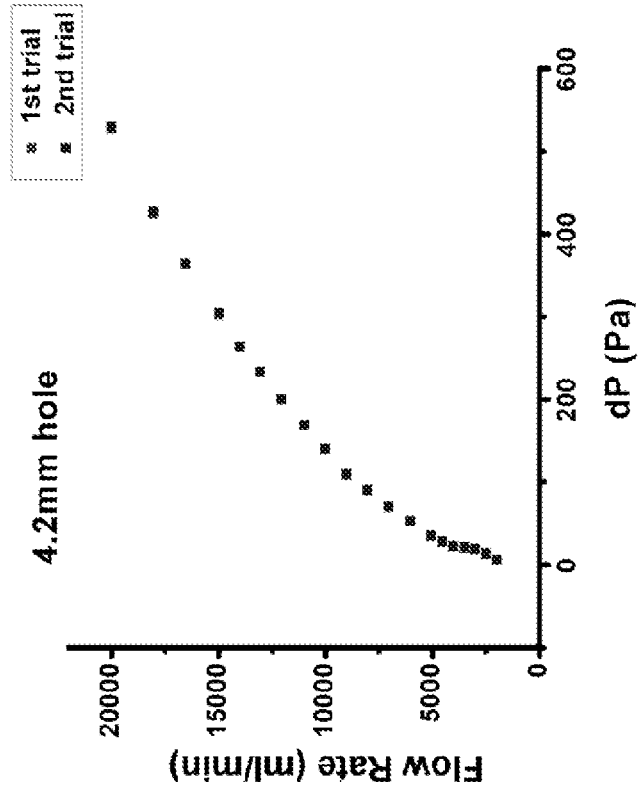
FIG. 4 shows an experimental calibration curve determined by measuring pressure difference across the orifice vs. volume flow rate.
Figure 5:
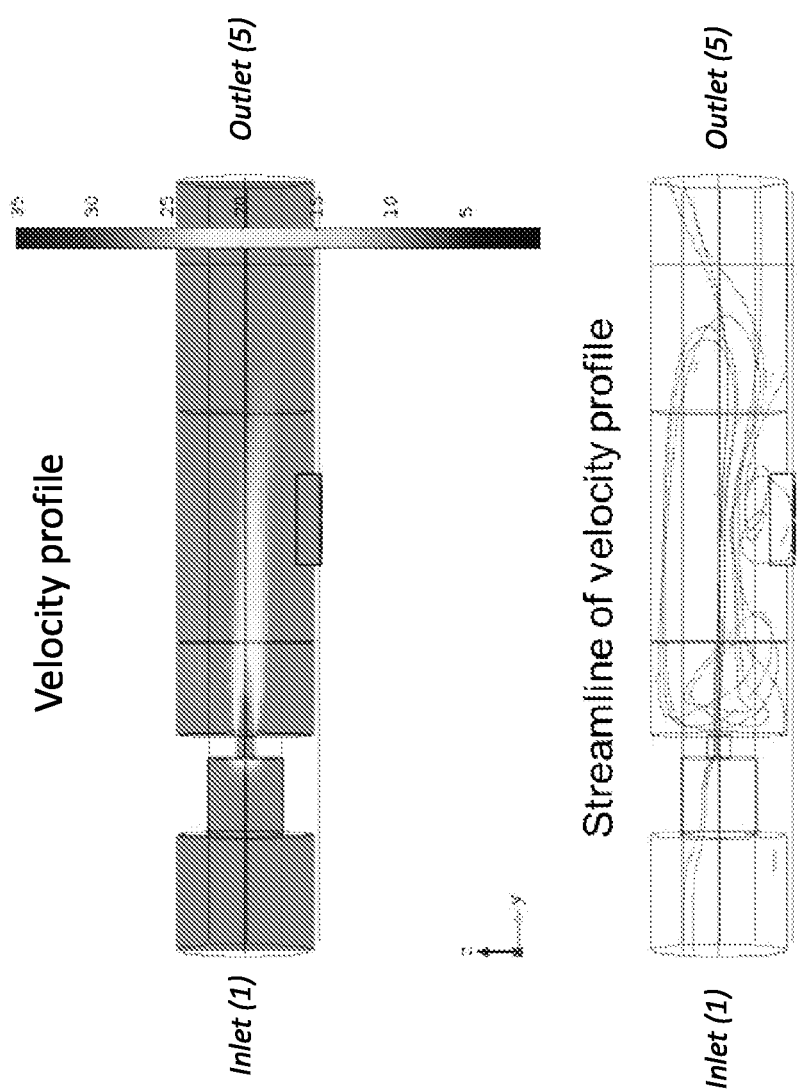
FIG. 5 shows a numerical simulation of the velocity profile (top) and streamline (bottom) of the flow path.
Figure 6:
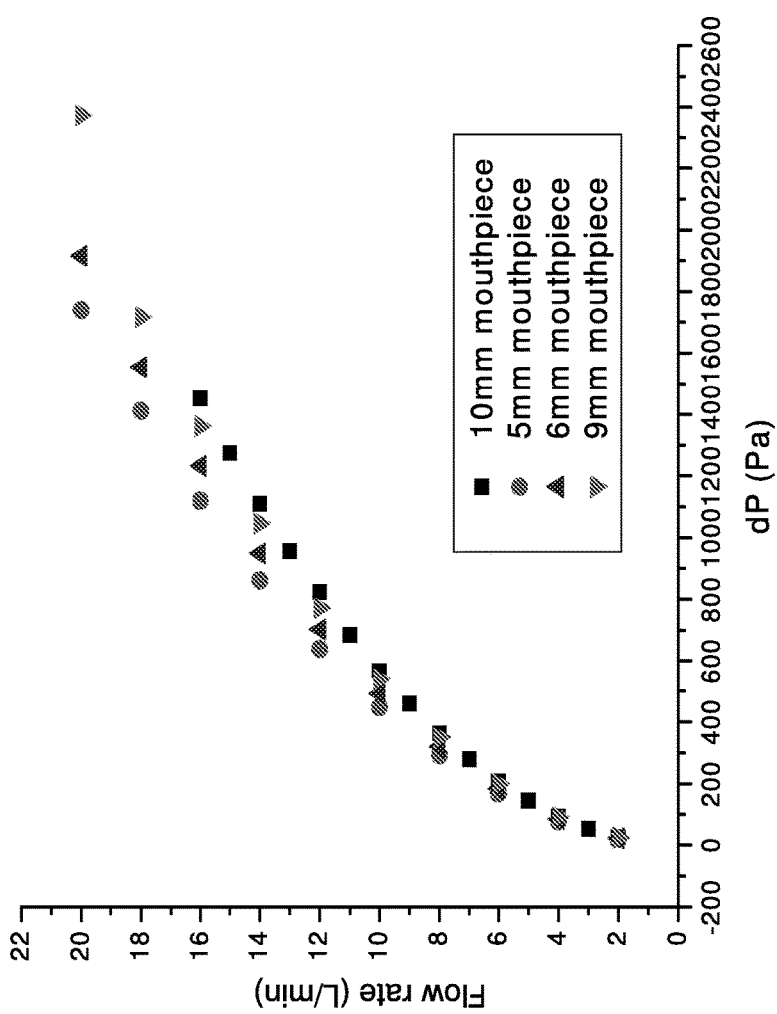
FIG. 6 shows a numerical simulation of the flow rate vs. pressure difference calibration curves with different cross sectional areas at the inlet of the pressure sensor, but a fixed cross sectional area of orifice (3 mm).

Referring now to FIG. 4, an experimental calibration curve determined by measuring pressure difference across the orifice vs. volume flow rate is shown. The diameter of the opening of the orifice is 4.2 mm. A calibration curve, shows dependence of backpressure on the flow rate. A single inlet pressure sensor can also be used. In this case, the inlet pressure is measured in reference to the ambient pressure.

The above analysis is correct only if the cross sectional areas at the positions of the inlet and outlet of the pressure sensor is larger than the cross sectional area of the orifice. This is because Eq. 1 assumes the flow velocity at the inlet is approximately zero compared to the velocity at the orifice, which is valid only of the sectional area at the inlet is much larger than that at the orifice. This conclusion is confirmed by numerical simulation shown in FIGS. 5 and 6. For an accuracy greater than 90%, the ratio of the cross sectional area at the inlet of the pressure sensor to the cross sectional area of the orifice should be greater than approximately 1.5.

Figure 7:
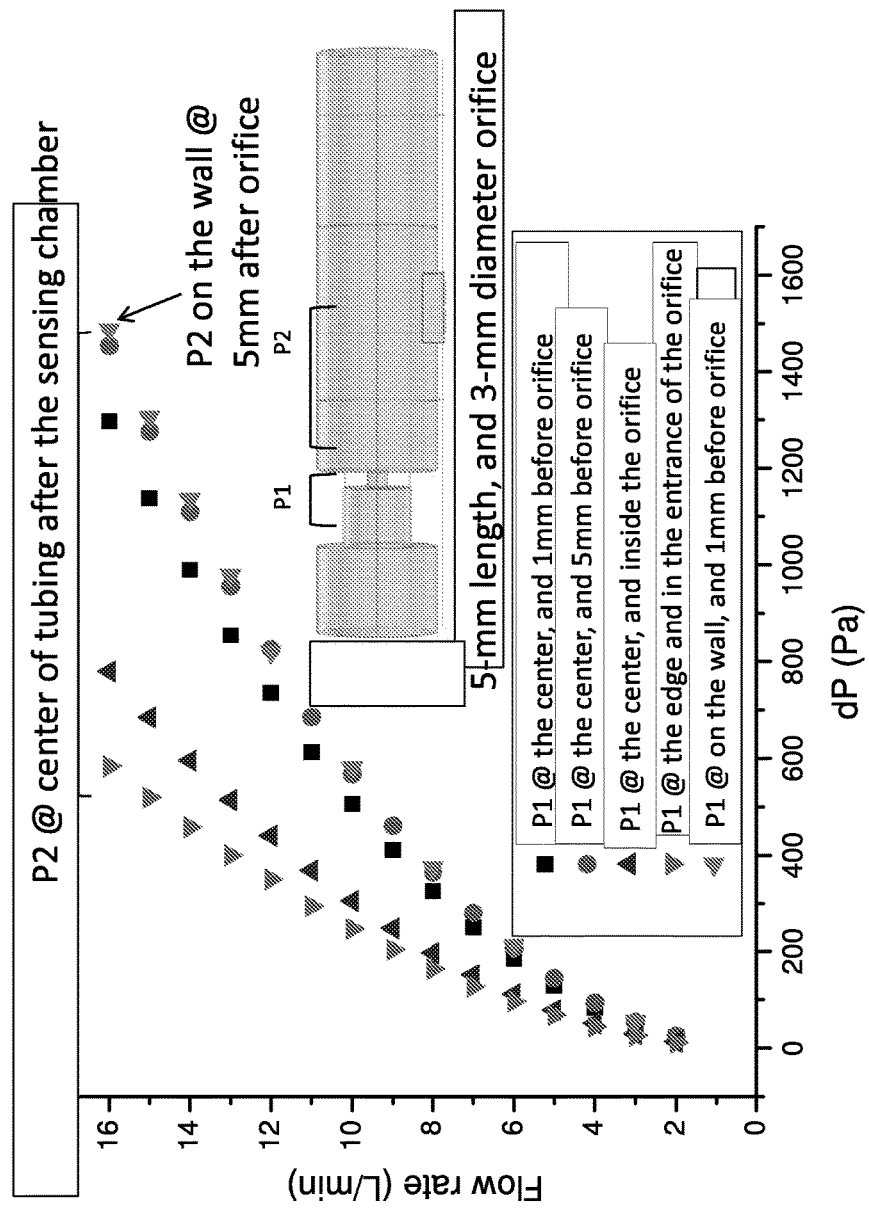
FIG. 7 shows a numerical simulation of the flow rate vs. pressure difference calibration curves with the pressure sensor inlet positioned at different locations of the flow path.

Referring now to FIG. 7, shown there is a numerical simulation of the flow rate vs. pressure difference calibration curves with the pressure sensor inlet positioned at different locations of the flow path. Maximum pressure reading (most accurate) can be obtained by placing the inlet of the pressure sensor at least 1 mm away from the orifice and on the wall of the device. Yet another requirement is the inlet of the pressure sensor is located substantially away from the orifice. This requirement further ensures that the flow velocity is close zero. Similarly the outlet of the pressure sensor should also be located substantially away from the orifice such that the flow velocity at the position of the outlet is also close to zero. This conclusion is confirmed by numerical calculation shown in FIG. 7.

Referring now to FIG. 8, an example of data illustrating dependence of normalized backpressure on the diameter of the orifice where the squares and diamonds correspond to the measured result and the calculated result from the Bernoulli equation, respectively is shown. For a low cost pressure sensor, the backpressure has to be large enough in order to be measured accurately. However, a large backpressure makes it difficult for users, especially children to blow into the breath analyzer. More importantly, a large backpressure requires one to blow hard into the flow path, which deviates from the resting condition, and thus introducing errors to the measured REE. Extensive experiments (diamonds), calculation with the Bernoulli's equation (square), and numerical simulations of backpressure vs. orifice size indicate the ideal diameter of the orifice is between 2.5 to 7 mm. If the diameter of the orifice is smaller than 2.5 mm, the backpressure will be too high to breathe comfortably. On the other hand, if the diameter of the orifice is greater than 7 mm, the pressure difference is too small to be measured with a low cost pressure sensor. This analysis is based on using a circular orifice, and another geometry (such as square) can also be used, but the cross sectional area of the orifice must be between 5-40 mm2.

Low cost pressure sensors are typically based on microfabricated MEMS (Micro-ElectroMechanical System) devices. These devices are known to be sensitive to their orientations relative to the gravitational direction of the earth. For accurate flow rate measurement, the pressure sensor should be oriented to minimize the effect of the earth gravity (e.g., the diaphragm is facing sideway).

c) REE Measurement—Temperature Correction:

The most widely used equation for determining REE from consumed oxygen and produced carbon dioxide is the Weir equation, which takes the form of $$REE\ (kCal/day)=[3.9\ (VO_2)+1.1\ (VCO_2)]\times 1.44, \quad (4)$$

where $VO_2$ is oxygen consumption rate (mL/min), and $VCO_2$ is carbon dioxide production rate (ml/min), respectively. $VO_2$ and $VCO_2$ can be further expressed in terms of $V_E$, and given by $$VO_2=V_E\times(0.2093-FO_2), \quad (5)$$

$$VCO_2=V_E\times(FCO_2-0.0003), \quad (6)$$

where $FO_2$ and $FCO_2$ are the fractions of oxygen and carbon dioxide in the exhaled breath.

Note that the Weir equation assumes that $V_E$ is obtained under the standard pressure, temperature and dry condition (STPD: temperature=0° C., pressure=760 mmHg and humidity=0%). In practice, it is more convenient to determine $V_E$ under a different condition, such as breath temperature and humidity. In the present invention, $V_E$ is determined at the point of the orifice, where the pressure is close to the atmospheric pressure, temperature is the breath temperature, and humidity is saturated (condensing) relative humidity condition (ATPS). In order to convert $V_E$ (ATPS) to $V_E$ (STPD), one must include a temperature (T) sensor near the orifice. Once the temperature near the orifice is determined, the relative humidity near the orifice can also be determined based on the calibration curve of relative humidity vs. temperature. From the temperature and relative humidity near the orifice (As shown in FIGS. 2, 3 and 9), one can determine $V_E$(STPD) from $V_E$(ATPS) by applying a correction factor.

d) REE Measurement—Water Condensation:

The disclosed apparatus measures REE by blowing breath directly into the apparatus, saliva and water condensation are thus of important concerns. Excessive amount of saliva entering the apparatus and water condensation in the apparatus raise hygiene issues, and may cause the failure of the apparatus. Existing commercial instruments have either specially designed mouthpieces with saliva-specific reservoirs (Ross, et. al., U.S. Pat. No. 7,108,569 B2), and/or additional mixer chambers to allow the breath to cool down to the ambient temperature (Orr, Kofoed, Durst, U.S. Pat. No. 6,475,158 B1; Robergs, et. al., US2004/0176698), and/or to remove humidity with nafion (Flanagan, PCT WO 2004/041084 A1).

In one useful example as illustrated, for example in FIG. 3, a filter (9) made of porous material, such as a nylon mesh or a felt, is introduced in the mouthpiece, which prevents saliva from entering the device, while allowing exhaled breath passing through without much backpressure. An alternative design of the mouthpiece is to include at least one one-way valve such that the user can breathe in but not to inhale air from the breath analyzer. To further minimize water condensation in the apparatus, a fan (8) is added to the breath analyzer, which is connected to the main flow path via a one-way valve (7) located parallel to the flow path to avoid interference with the normal resting breathing condition. The fan is off and the one-way valve is closed during REE measurement. After measurement, the fan turns on, with the on-way valve opened to allow air to flow into or out of the detection chamber, which helps dry out condensed water. It is worth noticing that while most of REE measurements require dehydration of breath sample to prevent excessive moisture built up in the system or vapor water interference with sensor measurement, the current REE measurement is compatible with breath condensing conditions.

Referring now to FIG. 10A and FIG. 10B, one example embodiment of the sensor cartridge design is shown. Included is a sensor cartridge (12) including a plurality of at least 2 sensing elements (213) and at least 2 reference elements (215). Each of the sensing elements comprises a sensing reference element with a grid structure (as best shown in FIG. 10B).

e) REE Measurement—Colorimetric Sensor Cartridge:

Tao and Forzani (US Publication No. 20130150746 A1, having publication date Jun. 13, 2013, incorporated here by reference) disclose a portable metabolic analyzer based on colorimetric sensing technology to measure REE. A key requirement in the colorimetric sensing technology is to coat a sensor cartridge or chip made of a solid material, such as plastics or glass, with chemical sensing materials uniformly. By simply coating a solid surface with a chemical solution, the distribution of the chemicals is often not uniform, due to effects, such as "coffee ring effect". To combat this problem, the present invention solved the problem by creating a patterned structure with certain depth on the surface of the sensor cartridge. The ideal size of the pattern includes at least 81 vertices and a depth of 20 to 200 microns. A specific design of the sensor cartridge comprises a plastic sheet, on which 4 areas of the patterned structure are created. Two of the areas are for oxygen, carbon dioxide sensing, and the remaining two for the corresponding reference corrections.

f) PAE Measurement—REE Based MET Algorithm:

In principle, if one can determine physical activity-related energy expenditure or PAE, it is then possible to obtain TEE by combining PAE with REE. Although various devices have been developed to monitor various activities, translating the recorded activities into daily physical activity energy expenditure, PAE, is a non-trivial task. This is because the actual energy expenditure for a fixed number of steps or floor counts depends on many factors, such as the person's weight, gender, age, speed, and intrinsic metabolic rate. A well-known concept is based on the MET-algorithm (Crouter, et. al. Med Sci Sports Exerc. 2010 May; 42(5): 1029-1037), which quantifies energy expenditure of physical activities in a unit of MET, where 1 MET is the person's REE. An energy expenditure rate of 2.5 METs means that the person's energy expenditure is 2.5 times of his/her REE for a particular activity. Obviously, the accuracy of this MET concept relies on the accuracy of REE value. Previously, the MET-algorithm has been used to determine PAE using REE value estimated from generic equations. These equations are developed based on the statistical average of large populations (W. D. McArdle, et al., "Exercise Physiology: Energy, Nutrition, & Human Performance," Lippincott Williams & Wilkins, 2007), which is known to be inaccurate because even people of the same gender, similar age and weight can have very different REE values due to factors, such as hormones, body composition, and medications (M. Manore, N. Mayer, and J. Thompson, "Sport Nutrition for Health and Performance," Human Kinetics, Champaing, Ill., 2009). Furthermore, the REE of a person may vary over time, especially during weight loss program.

In the present invention, it is the measured REE of an individual, rather than a calculated REE, that is used to determine PAE. This invention naturally takes into account weight, age, gender and other personal information in the algorithm of determining PAE from the type, intensity and duration of tracked physical activities. Accelerometers and/or other physical activity sensors are used to record activities and identify the type of activity and time spent in a specific activity. The information is qualitatively used for accurate assignment of MET equivalents, and calculation of PAE using equation, $$\text{PAE (kcal/day)} = \Sigma X_{activity_i} EE_i, \quad (7)$$

where $EE_i$ is the energy expenditure for an activity given by $EE_i = MET_i \times REE$ ($MET_i$ is the MET of the activity), and $X_{activity_i} = t_{activity_i}/24$ hrs is the fraction of daily time spent on a particular activity assessed by the physical sensor. Using this algorithm, PAE and TEE are determined (FIG. 10).

Note that for physical activities that cannot be tracked with a physical sensor, speech recognition methods can be applied. However, to minimize the burden on the user, only the change in, rather than the total amount of, the physical activities is recorded.

g) Calorie Intake—Behavioral Change Algorithm:

Accurate tracking of calorie intake is difficult because the calorie for a certain type of food depends not only on the size but also ingredients of the food, which vary from restaurant to restaurant, and from family to family. Tracking food intake every meal and every day is tedious and impractical for most people. Instead of tracking total calorie intake, the present invention discloses a method to focus on the change of food intake. For example, if the user consumes a hamburger, or a can of soda less than his/her regular daily portion, the projected amount of calorie and weight reduction per year will be displayed, and encouraging messages, such as project weight reduction, prolonged lifespan, and other health benefits will pop up. Likewise, if the user consumes a hamburger, or a can of soda more than his/her regular daily portion, the projected amount of calorie_and weight increase per year will be displayed, and warning messages will pop up to discourage the user's behavior. This method reduces the users' burden from tracking single-food item consumption, and makes it easier to track the change using speech recognition. An additional benefit of the present method is to provide motivations for positive behavioral change, and discourage negative behavioral change. The present invention also allows the user to set up a weight goal (target weight and target date), and recommends the needed calorie intake change in order to reach the goal.

h) Personalized Recommendation of Physical Activity Time Based on REE:

The present invention also discloses an additional algorithm to recommend the time duration (e.g. daily minutes) of physical activities (walking, running, etc.) needed to achieve the above mentioned target weight. The recommendation is based on the type of activity, and the measured REE for the user with the following formula, $$\text{Time duration (min/day)} = \{[(WT_t - WT_o) \times 3500 \text{ (kCal/lbs)}/(\text{date}T - \text{date}_o)] - \text{PAEexcIREE (kCal/day)} + \Delta CI \text{ (kCal/day)}\} \times (24 \text{ hs/day}) \times (60 \text{ min/h})/\{MET \times REE\}, \quad (7)$$

where $WT_t$ and $WT_o$ are target and current weights in lbs or $K_g$, respectively, dateT and date$_o$ are target and current dates, respectively; $PAE_{excIREE}$ is daily physical activity energy expenditure (excluding REE); $\Delta CI$ is daily calorie intake change (a negative value of ΔCI means calorie reduction, and a positive value means calorie increase); MET is the metabolic equivalent for a chosen preferred activity (e.g. normal walking, brisk walking, running, etc.); and REE is the individual's measured REE. $PAE_{excIREE}$ and ΔCI are included in the time calculation if they are available from REE-based MET algorithm, and calorie intake change information.

i) Metabolic Age:

The present invention also discloses methods and strategies to interpret the measured REE. As mentioned before, REE is the energy that the body needs to maintain basic metabolic functions, such as breathing, blood circulation, brain activity, and cell regeneration. For persons of same gender, weight, and height, it has been statistically proven that REE decreases with increase of age due to decreasing metabolic functions. Normalized REE given by $$\text{Normalized REE (Kcal/(h} \times \text{m}^2\text{))} = \text{REE (kCal/day)}/(24 \text{ h} \times \text{SBA (m}^2\text{))} \quad (8)$$

$$\text{with SBA (m}^2\text{)} = (\text{height})^{0.725} \times (\text{weight})^{0.425} \times 71.84, \quad (9)$$

has been tabulated by gender, and associated to age segments (Fleish A., Le metabolism basal standard et sa determination au moyen du "Metabocalculator", Helv Med. Acta, 1951, 18:23). Due to the lack of REE measurement tools in the past, Normalized REE has not been widely used. The present invention uses Normalized REE measured over time to calculate Time-Averaged Normalized REE of the user, which provides an estimate of the user's metabolic age. In addition, Normalized REE, and metabolic age are used in the algorithm of the present invention to provide specific recommendations to enhance metabolic rate, and decrease metabolic age.

One preferred embodiment includes three major components, 1) a metabolic analyzer that measures metabolic rate, 2) a cellphone or tablet that communicates with the metabolic analyzer for data processing, storage and display, and 3) a cloud that communicates with the cellphone or tablet for data storage and further processing. Here the metabolic analyzer, cellphone or tablet and cloud include hardware as well as associated software and/or firmware.

Metabolic Analyzer Elements

Referring now to FIG. 9, one embodiment of a side view of a metabolic analyzer device flow path structure. The metabolic analyzer device 90 includes light source (10), sensor cartridge (12), photo-diodes (13), electronic circuit board (14) and battery (15) is shown. The metabolic analyzer 90 itself includes 5 major components, a mouthpiece (15), a flow path structure (100), a detection chamber (110), a circuit board (14), a housing (not shown) and a battery with associated charging circuit (115).

The mouthpiece (15) in the metabolic analyzer is connected to one end of the flow path structure to allow the user to blow into the flow path structure. In one embodiment, the mouthpiece contains a filter made of porous material, such as nylon mesh or felt, to prevent saliva from entering the flow path without creating substantial backpressure. In another embodiment, the mouthpiece at least one one-way such that the user can breathe into the breath analyzer but not inhale from the breath analyzer. The one-way valve also helps to prevent saliva from entering the breath analyzer. An additional one-way valve can be used to allow the user to inhale from the ambient via the mouthpiece.

The flow path structure comprises, a thermistor, a specially designed orifice structure and a detection chamber. The thermistor is located near the orifice (on the inlet side) that reads the temperature of the breath at the orifice. The flow rate of the breath (VE) is measured with the orifice along with a pressure sensor, together known as flow sensor. The pressure sensor is operated in differential mode allowing correction due to pressure offset such as difference in atmospheric pressures due to location differences. The specially designed orifice structure enables sensitive and accurate differential pressure measurements to be made without incurring the use of an expensive pressure sensor or additional components to achieve high fidelity flow measurements with minimal backpressure as felt by the user. The system in place to ensure low backpressure is herein referred to as backpressure control, which preferably is an intrinsic part of the sample inlet, or even part of the flow sensor, but can also be a separate entity. One of the keys in accurate and reliable resting metabolic measurement and burden-free metabolic measurement is to allow the user to breathe freely. In this regard, minimal backpressure is required. The flow measurement technology disclosed in the present invention minimizes the backpressure felt by the user by maximizing differential pressure signal detected by the pressure sensor, thus, allowing low cost commercially available pressure sensor to be used in the disclosed breath analyzer. Other embodiments to address this issue include using a more sensitive pressure sensor, using multiple pressure sensors, or using an intelligent sampling scheme where periodic baseline measurements can be made.

The detection chamber (FIGS. 3 and 9) is an enclosed volume that houses the sensor cartridge (12), and an optical system consisting of a light source (10) and an array of photodiodes (13). The optical system performs colorimetric test on the sensor cartridge, which allows determination of the consumed oxygen rate and produced carbon dioxide rate. A fan is designed to remove water vapor and condensation from the detection chamber.

Circuit board: Mounted on the circuit board are a pressure sensor, an array of photodiode detectors, microprocessors, Bluetooth and various other circuit elements for signal transduction, processing and transmission in a conventional fashion. The flow path structure is mounted on top of the circuit board such that the sensing elements on the sensor cartridge are placed directly on top of the photodiode array. A pressure sensor is mounted on the circuit board but with its inlet and outlet connected to the two sides of the orifice. The sample outlet provides a way to properly exhaust the sampled breath.

Operation of the metabolic analyzer: The exhaled breath from the mouthpiece, which is resulted from adaptive sampling mechanism, is first directed through the orifice, and then to the detection chamber for analysis. After that, the breath sample is directed out of the metabolic analyzer. During metabolic rate measurement, the fan is off and the one-way valve is closed so that ambient air cannot enter the detection chamber via the fan to interfere with the analysis of breath sample. After the measurement is completed, the fan is on, which opens the one-way valve to dry out the detection chamber.

Battery and charging circuit: The battery may advantageously be a high energy-density lithium ion battery, which is rechargeable with a charging circuit. The battery energy level and charging status are monitored and displayed.

Housing: A housing made of plastics or aluminum is used to house the flow path structure, detection chamber, circuit board, LED display, switch, battery and associated charging circuit.

Figure 11:
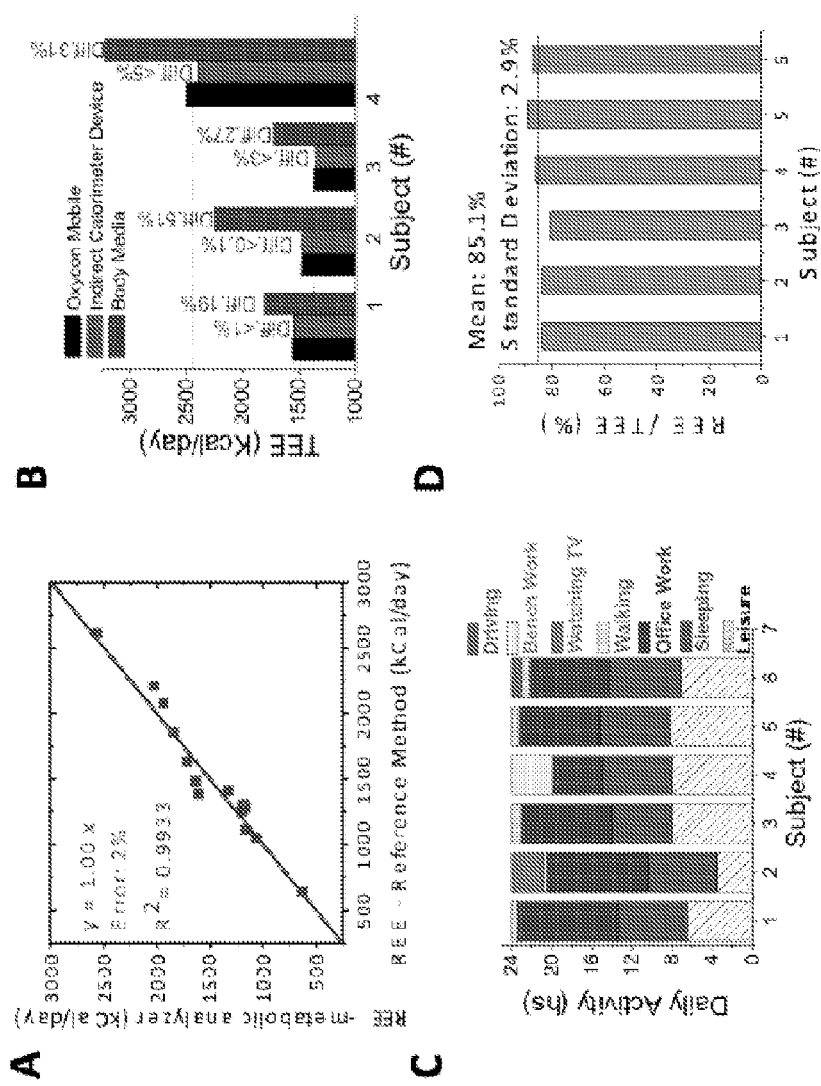
FIG. 11A-FIG. 11D show data representing clinical validation of the metabolic analyzer with different methods.

Referring now to FIG. 11, clinical validation of the metabolic analyzer with different methods are shown. (A)

Validation with Douglas Bag Method: comparison of resting energy expenditure (REE) assessed by the metabolic analyzer vs. that by the Douglas reference method. (B) Validation with Reference instrument: Comparison of total energy expenditure (TEE) values assessed in 4 sedentary lifestyle individuals with the metabolic analyzer with FDA-approved commercial Oxycon Mobile instrument (black), and a second commercial device (based on accelerometer, skin conductance and skin thermal flow detection). The metabolic analyzer agrees with the Oxycon Mobile (FDA-approved indirect calorimeter instrument) within <5% error (indicated as Diff.). (C) Daily activity distributions of 6 subjects for a typical day. The energy expenditure for each activity was measured and combined with the corresponding time and frequency for each activity to determine TEE. (D) The REE/TEE ratios for all subjects, which show that REE represents an average of 85% of TEE for the subjects. The result illustrates the importance of accurate assessment of REE.

Figure 12:
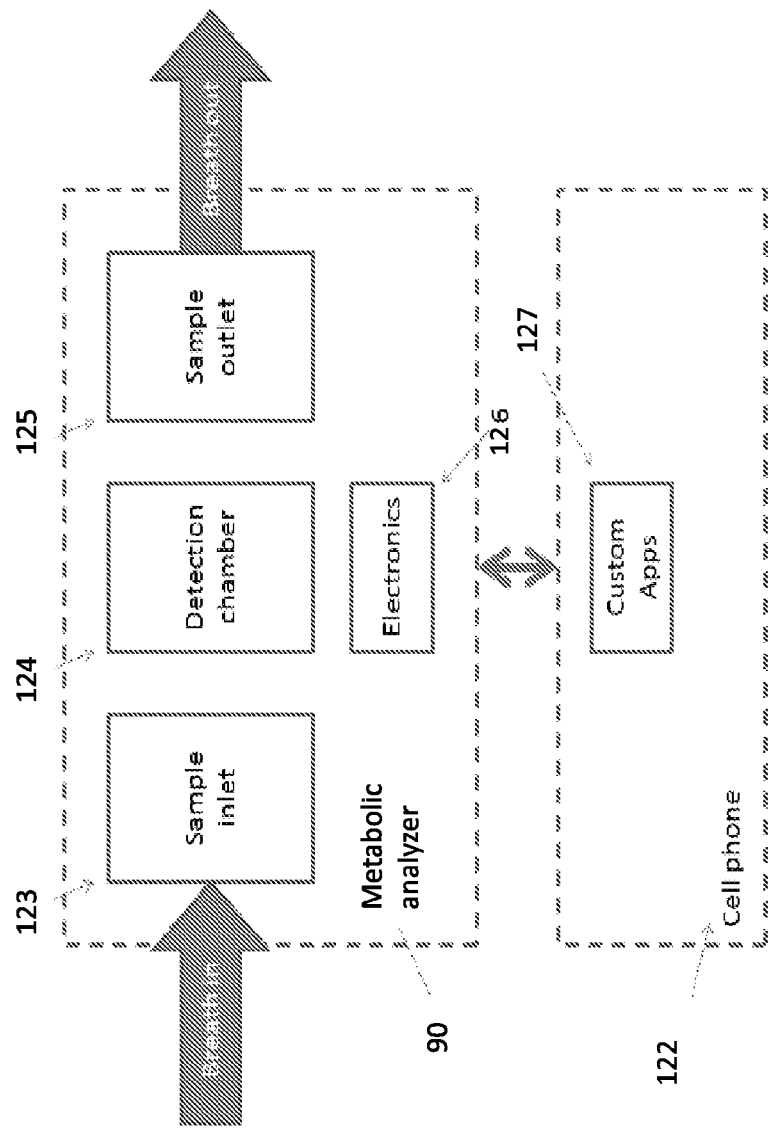
FIG. 12 is a schematic diagram illustrating one embodiment of the system, including a metabolic analyzer and cell phone.
Figure 13:
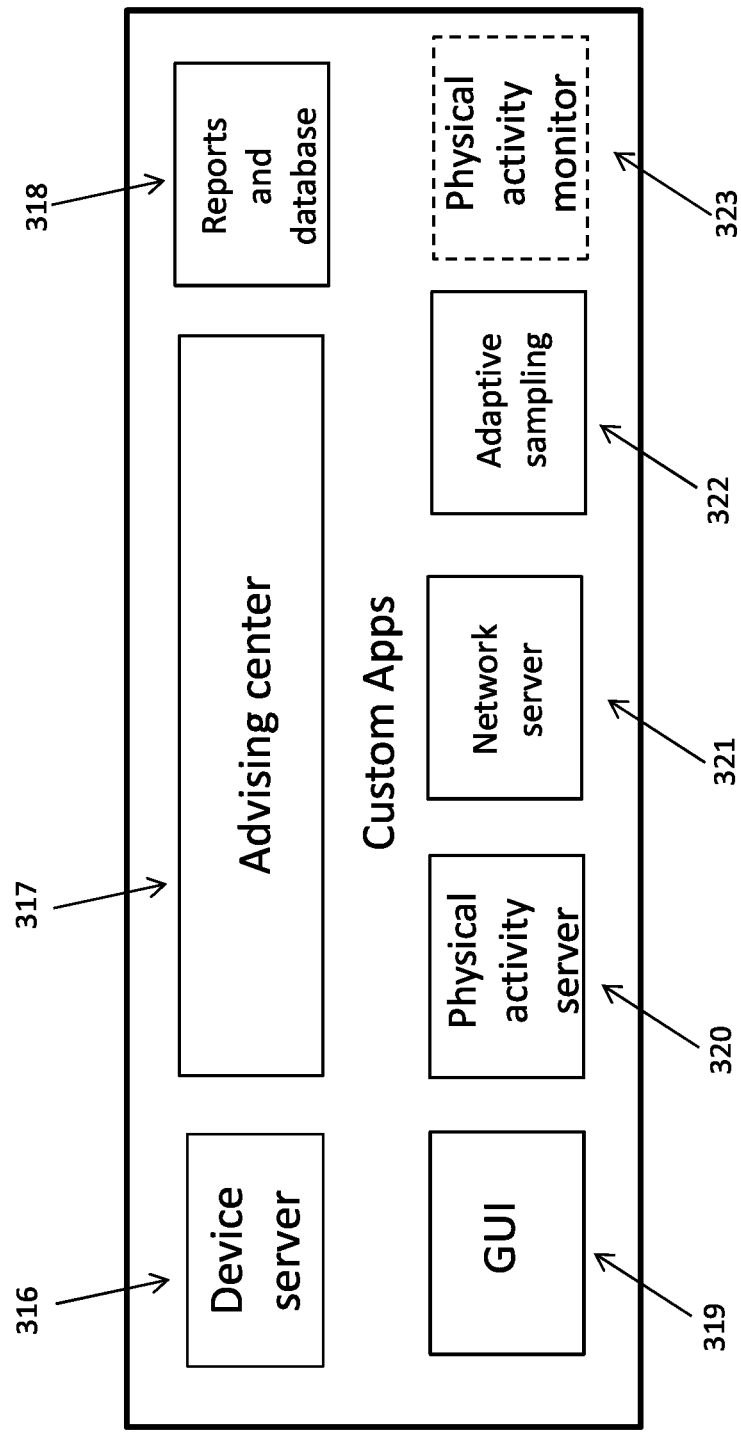
FIG. 13 is a schematic diagram illustrating one embodiment of the custom App portion of the metabolic analyzer system.

Referring now to FIG. 12 a schematic diagram illustrating one embodiment of the system, including a metabolic analyzer and cellphone is shown. Referring now also to FIG. 13, a schematic diagram illustrating one embodiment of the custom App portion of the metabolic analyzer system. Another major component of the metabolic analyzer system is the cell phone or tablet (122) (see FIGS. 12 and 13). Referring specifically now to FIG. 12, the system includes a A custom App (marked 127 on FIG. 12) is used to perform a number of useful tasks as indicated with reference to FIG. 13.

First, the App allows communication with the device (121) such as receiving data from the device, pairing to an available Bluetooth of the device, reporting statuses between the device and the cell phone or tablet, etc.

Second, the App performs analysis, organize results, process data, evaluate progress, store and retrieve data (318).

Third, the App allows a user to interface with it as indicated by GUI (319) providing a means to enter users' information, targets/goals, make decisions for data transmission, receive information/recommendations, perform searches in the database, obtain graphical presentations and so on. Unlike some user interfaces, this particular embodiment consists of a speech recognition component to allow user to enter information verbally. A voice decoder program converts the voice into text where a search engine function automatically extracts the amount of calorie reduction (or addition) which is previously determined from established online databases.

Fourth, the App includes an advising center (317) where coaching advices and recommendations for weight management, metabolic rate, exercise, dietary intakes and weight gain/loss goals are generated.

Fifth, the App also functions as a physical activity server (320) where physical activity monitors are being serviced similar to the metabolic analyzer device mentioned above. This is particularly useful in the weight and metabolic management, and is considered an integral part of the metabolic analyzer system. The physical activity monitor (323) can be a physically separate entity similar to the metabolic analyzer device, or it can be a separate App, or an integral part of the current App. The use of an App as physical monitor can take advantage of the prevalent habit of people carrying smartphones in their pockets, thus helps ensure accurate data for assessment of total energy expenditure (TEE). One such embodiment can be employing the two built-in sensors of the phone: First, a 3-D accelerometer to monitor energy expenditure from routine translational motion activities such as walking and running; second, a pressure sensor adapted as an altimeter to measure climbing activities (e.g. stairs or hiking). These sensors will provide not only energy expenditure data, but also the number of steps and climbed levels (floors), encouraging users to walk and take the stairs. Energy expenditure will then be calculated using data from the physical activity sensor array together with an energy expenditure algorithm based on REE-MET concept.

Sixth, the App serves as a network server for wireless communication (321). In addition to the ability to connect wirelessly via a Bluetooth to the device and/or other physical activity sensors, the App allows the cell phone to wirelessly connect to the internet or cloud and eventually communicate with a remote server, which in turn may retransmit to another server, a web site, database, or emails, text messages accordingly.

Seventh, the App has an adaptive sampling (322) component to help guide users breathe naturally and comfortably in order to obtain a reproducible and accurate basal metabolic rate. The method consists of musical guidance for natural and regular breathing, and starts with the first breathing cycle of the subject into the device. An algorithm that analyzes the first two breathing cycles determines the breathing frequency. After the breathing frequency is determined music tone/progressing graphics with a rhythm matching the subject breathing frequency is/are played/shown. All of the required processes are performed in real-time and adapted throughout the test, given the pace of the music/graphics/mechanical vibrations is/are modified in accordance with the user's actual breathing frequency.

Eighth, the App has an algorithm based on REE measurement to help guide users to perform physical activity time to meet the goals (e.g. target weight and target date). If information is available, the algorithm takes into account physical activity recorded from the user using physical sensors, and calorie intake reduction or addition recorded with the app. All of the required processes are provided as an instant feedback to the user.

Overall Operation of the System

First, the device and the cell phone or tablet is to be turned on. If there are other optional devices to be connected, they can also be turned on. After that, the customized App on the cell phone or tablet for the metabolic analyzer is launched. The device and the cell phone or tablet should be paired via the Bluetooth before connecting and the connection can be made after the App is launched, at which point, the breath test commences. The user is to exhale through the mouthpiece of the device and the breath sample is collected and calorimetric analysis is performed. As the user starts to breathe into the device, music/graphics will be played/shown at a pace that aims at subconsciously guiding the user to breathe naturally and comfortably to improve the reproducibility and accuracy of the test.

The test results will be sent to, processed, and displayed on the cell phone or tablet. In addition, user can also access history, specify their weight management or metabolic goals, access advising center where encouragements and/or advices are provided to help the user achieve their personal goal. The users will further have the option to send their data to healthcare/fitness professionals or upload their progresses to social networking sites. In addition, if other physical activity modules are available, the user can also access the information or connect to them via the same App and the App, once linked to the physical activity monitors (either in the form of another App or another physical device), will be able to automatically upload the physical activity data to be used in the advising center for more accurate assessment on energy balance. Furthermore, the user will be able to assess estimations of time of a particular activity (e.g. normal walking, brisk walking, running, etc.) to reach specific target weight and date, based on their REE measure, and available information of PAE and diet calorie change.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The following publications are incorporated by reference.

Internet Web Sites 1. http://www.fitbit.com/
2. http://www.carefusion.com/medical-products/respiratory/cardio-pulmonary-diagnostics/metabolic-carts-cpet-nutrition/metabolic-carts/oxycon-mobile.aspx
3. http://www.bodymedia.com/
4. http://www.actigraphcorp.com/
5. http://www.diabetesaustralia.com.au/PageFiles/763/Primarypreventingguideline.pdf U.S. Patent Documents 1. Mault et al. U.S. Pat. No. 6,468,222 B1 issued on Oct. 22, 2002;
2. Mault, U.S. Pat. No. 4,917,108 issued on Apr. 17, 1990;
3. Mault, U.S. Pat. No. 5,038,792 issued on Aug. 13, 1991;
4. Mault, U.S. Pat. No. 5,178,155 issued on Jan. 12, 1993;
5. Mault, U.S. Pat. No. 5,179,958 issued on Jan. 19, 1993;
6. Mault, U.S. Pat. No. 5,836,300 issued on Nov. 17, 1998;
7. Mault, U.S. Pat. No. 7,392,193 issued on Jun. 24, 2008;
8. Mault, U.S. Pat. No. 6,478,736 B1 issued on Nov. 12, 2002;
9. Mault, US Patent publication No. US 2004/0254501 A1 published on Dec. 16, 2004;
10. Harnoncourt, U.S. Pat. No. 5,419,326 issued on May 30, 1995;
11. Harnoncourt et al., U.S. Pat. No. 5,503,151 issued on Apr. 2, 1996;
12. Harnoncourt et al., U.S. Pat. No. 5,645,071 issued on Jul. 8, 1997;
13. Harnoncourt, U.S. Pat. No. 5,647,370 issued on Jul. 15, 1997
14. Delsing, U.S. Pat. No. 5,796,009 issued on Aug. 18, 1998;
15. Brugnoli, U.S. Pat. No. 6,206,837 issued on Mar. 27, 2001;
16. Brugnoli, U.S. Pat. No. 4,658,832 issued on Apr. 21, 1987;
17. Brugnoli, U.S. Pat. No. 4,631,966 issued on Dec. 30, 1986;
18. Kofoed, Orr, Rich, U.S. Pat. No. 5,789,660 issued on Aug. 4, 1998;
19. Orr, et. al., US Patent publication No. US2010/0036272 A1 published on Feb. 11, 2010;
20. Mace, et. al, US Patent publication No. US2002/0029003 A1 published on Mar. 7, 2002
21. W. J. Sullivan, G. M. Peters, P. L. Enright, "Pneumotachographs: Theory and Clinical Application", respiratory Care, July 1984, Vol. 29-7, pp. 736-49
22. Orr, Kofoed, Durst, U.S. Pat. No. 6,475,158 B1 issued on Nov. 5, 2002
23. Conradie, Du Preez P T C, WO 2010/143027 A1 Published on Dec. 16, 2010;
24. Ross, et. al., U.S. Pat. No. 7,108,659 B2 issued on Sep. 19, 2006;
25. Robergs, et. al., US Patent Publication No. US2004/0176698 published on Sep. 9, 2004;
26. Flanagan, PCT Publication No. WO 2004/041084 A1 published on May 21, 2004;
27. Kofoed-Orr et al.
28. Knowler W C, Barrett-Connor E, Fowler S E, Hamman R F, Lachin J M, Walker E A, et al. Reduction in the incidence of type 2 diabetes with lifestyle intervention or metformin. N Engl J Med. 2002 Feb. 7; 346(6):393-403.
29. Scott E. Crouter, 1 Erin Kuffel, 2 Jere D. Haas, 3 Edward A. Frongillo, 4 and David R. Bassett, Jr., A Refined 2-Regression Model for the ActiGraph Accelerometer, Med Sci Sports Exerc. 2010 May; 42(5): 1029-1037
30. W. D. McArdle, et. al., "Exercise Physiology: Energy, Nutrition, & Human Performance," Lippincott Williams & Wilkins, 2007
31. M. Manore, N. Mayer, and J. Thompson, "Sport Nutrition for Health and Performance," *Human Kinetics, Champaing, Ill.,* 2009
32. Fleish A., Le metabolism basal standard et sa determination au moyen du i. "Metabocalculator", Helv Med. Acta, 1951, 18:23)

What is claimed is:

1. A system for measuring and tracking metabolic rate comprising:
    a mouthpiece having an inlet for the introduction of exhaled breath into a flow path;
    wherein the mouthpiece includes at least one orifice with a cross sectional area in the range of 4 $mm^2$ to 40 $mm^2$ in the flow path, and where the orifice is at least 50% smaller than the inlet cross sectional area;
    a colorimetric sensor providing a first output signal representing chemical measurements;
    a differential pressure sensor with a sensor inlet located on the inlet side of the orifice, where the differential pressure sensor provides a second output signal representing pressure measurements; and
    an adaptive sampling mechanism to detect and learn the user's natural breathing pattern to assist the user to perform consistent measurement, and to determine resting energy expenditure from pressure and chemical measurements, with pre-determined calibration curves that relate the first output signal representing chemical measurements to the chemical concentrations and the second output signal representing pressure measurements.

2. The system of claim 1 wherein the adaptive sampling mechanism
    resides in a processor, where the processor is adapted to play audio with a rhythm and volume, or video with motion sequence, where the rhythm and volume or motion sequence is adjusted to the pre-determined natural breathing pattern.

3. The system of claim 2 wherein the adaptive sampling mechanism further operates
    to detect changes in the breathing pattern over time;

to memorize changes in the breathing pattern over time; and to adjust the audio rhythm and volume or video motion sequence according to the changes in the breathing.

4. The system of claim 2 wherein the adaptive sampling mechanism further operates
to detect breathing patterns; and
to memorize breathing patterns.

5. The system of claim 2 wherein the adaptive sampling mechanism further operates
to detect breathing patterns;
to memorize breathing patterns;
to detect time intervals in which the breathing pattern is regular; and
to determine volume flow rate based on the data acquired during the time intervals.

6. The system of claim 1 wherein the sensor inlet is located at least 1 mm away from the orifice.

7. The system of claim 1 wherein the differential pressure sensor is mounted with an orientation at which the pressure reading is least dependent on earth gravity.

8. The system of claim 1 wherein the adaptive sampling mechanism operates to determine the resting energy expenditure curve with the Weir equation using at least measured exhaled volume flow rate.

9. The system of claim 1 further comprising a fan connected to the flow path to dry out water from condensation in the apparatus.

10. The system of claim 9 wherein the fan is connected to the flow path via a one way valve.

11. The system of claim 1 wherein the flow path comprises a detection chamber where at least one gas component in the exhaled breath is detected.

12. The system of claim 11 wherein the detection chamber comprises:
at least one light emitting diode;
at least one photodiode detector;
a colorimetric sensor cartridge holder; and
a colorimetric sensor cartridge inserted into the sensor cartridge holder.

13. The system of claim 12 wherein the colorimetric sensor cartridge comprises:
a solid surface;
a patterned structure in at least one area of the solid surface; sensing chemicals coated onto the area;
a reference area for signal correction; and
a notch design for positioning.

14. The system of claim 13 wherein the patterned structure comprises at least 81 vertices, and a depth between 20 µm and 200 µm.

15. The system of claim 12 wherein the distance between the top surface of the sensor cartridge and the top surface of the photo diode detector is less than 5 mm.

16. The system of claim 11 wherein a fan is attached to the detection chamber via a one-way valve.

17. The system of claim 1 further comprising a filter positioned between a user's mouth and the inlet of the flow path to prevent saliva of from entering the flow path while allowing breath to pass through.

18. The system of claim 1 further comprising a physical activity monitor residing in a processor that operates to determine activity-related energy expenditure from the physical activities and a measured resting energy expenditure of the user.

19. The system of claim 18 wherein at least a portion of the physical activities are provided into the processor via a speech recognition algorithm.

20. The system of claim 18 wherein the processor further operates to track a change in the food and beverage intake over the previous day, and provides calorie change associated with the food and beverage intake change.

21. The system of claim 20 wherein the processor includes speech recognition.

22. The system of claim 18 wherein the physical activity monitor further operates to provide time durations and intensities of physical activities.

23. The system of claim 20 wherein the adaptive sampling mechanism operates to provide recommendations to the user to reach a target weight at a target date based, at least, on the measured resting energy expenditure.

24. The system of claim 18 further comprising a means to provide recommendations of time duration of physical activities based at least on the measured resting energy expenditure.

25. The system of claim 20 wherein the adaptive sampling mechanism operates to determine normalized resting energy expenditure based on the resting energy expenditure and physical parameters of the user, including weight and height.

26. The system of claim 25 wherein the adaptive sampling mechanism operates to determine a physiological index that indicates the user's health or fitness status by comparing the measured normalized resting energy expenditure of the user with that of the populations.

27. A system for measuring and tracking metabolic rate comprising:
a mouthpiece having an inlet for the introduction of exhaled breath into a flow path;
wherein the mouthpiece includes at least one orifice with a cross sectional area in the range of 4 $mm^2$ to 40 $mm^2$ in the flow path, wherein the flow path comprises a detection chamber where at least one gas component in the exhaled breath is detected and where the orifice is at least 50% smaller than the inlet cross sectional area;
wherein the detection chamber comprises:
at least one light emitting diode,
at least one photodiode detector providing a first output signal representing chemical measurements,
a colorimetric sensor cartridge holder, and
a colorimetric sensor cartridge inserted into the sensor cartridge holder;
wherein the colorimetric sensor cartridge comprises:
a solid surface,
a patterned structure in at least one area of the solid surface,
sensing chemicals coated onto the area,
a reference area for signal correction, and
a notch design for positioning;
a differential pressure sensor with a sensor inlet located on the inlet side of the orifice, where the differential pressure sensor provides a second output signal representing pressure measurements; and
an adaptive sampling mechanism that operates to accurately determine resting energy expenditure from pressure and chemical measurements with pre-determined calibration curves that relate the first output signal representing chemical measurements to the chemical concentrations and the second output signal representing pressure measurements.

28. The system of claim 27 wherein the patterned structure comprises at least 81 vertices, and a depth between 20 µm and 200 µm.

* * * * *